(12) United States Patent
Hackel et al.

(10) Patent No.: US 8,780,190 B2
(45) Date of Patent: Jul. 15, 2014

(54) DENTAL INTRA-ORAL CAMERA

(75) Inventors: Andre Hackel, Biberach (DE); Florian Bühs, Berlin (DE); Heinz Lehr, Berlin (DE); Stephen Schrader, Kleinmachnow (DE)

(73) Assignee: Kaltenbach & Voigt GmbH, Biberach (DE)

( * ) Notice: Subject to any disclaimer, the term of this patent is extended or adjusted under 35 U.S.C. 154(b) by 807 days.

(21) Appl. No.: 12/812,938

(22) PCT Filed: Jan. 14, 2009

(86) PCT No.: PCT/EP2009/000182
§ 371 (c)(1),
(2), (4) Date: Jun. 3, 2011

(87) PCT Pub. No.: WO2009/090051
PCT Pub. Date: Jul. 23, 2009

(65) Prior Publication Data
US 2011/0234781 A1 Sep. 29, 2011

(30) Foreign Application Priority Data

Jan. 14, 2008 (DE) .......................... 10 2008 004 146
Jul. 1, 2008 (DE) .......................... 10 2008 031 054

(51) Int. Cl.
*A61B 1/24* (2006.01)
*A61M 5/172* (2006.01)
(52) U.S. Cl.
USPC .............................................. 348/66; 604/19

(58) Field of Classification Search
USPC ............................................................ 348/66
See application file for complete search history.

(56) References Cited

U.S. PATENT DOCUMENTS

| 1,984,544 | A | * | 12/1934 | Julius Pearlman | ............ 359/827 |
| 4,515,457 | A | * | 5/1985 | Harvey | ........................ 396/235 |
| 5,528,432 | A | * | 6/1996 | Donahoo | ........................ 359/894 |
| 5,702,249 | A | * | 12/1997 | Cooper | ........................... 433/29 |
| 2003/0107652 | A1 | * | 6/2003 | Williams | ................. 348/207.99 |
| 2007/0247691 | A1 | * | 10/2007 | Obrebski et al. | .............. 359/228 |
| 2008/0192124 | A1 | * | 8/2008 | Nagasaki | ................. 348/208.11 |

FOREIGN PATENT DOCUMENTS

| DE | 29824899 U1 | 6/2003 | |
| DE | 000029824899 U1 | * 6/2003 | .............. A61B 1/00 |
| EP | 1058860 A1 | 12/2000 | |

OTHER PUBLICATIONS

International Search Report for PCT/EP2009/000182 dated Jul. 3, 2009.

* cited by examiner

*Primary Examiner* — Sath V Perungavoor
*Assistant Examiner* — Howard D Brown, Jr.
(74) *Attorney, Agent, or Firm* — Marshall, Gerstein & Borun LLP

(57) ABSTRACT

The invention relates to an intra-oral camera having an imaging system for depicting the object located in front of an observation window of the camera on a recording unit, wherein the imaging system has at least one focusing unit for setting a suitable focus and an aperture unit for forming a variable aperture. The setting of the aperture is carried out independently of the focus adjusted by the focusing unit.

21 Claims, 5 Drawing Sheets

DENTAL INTRA-ORAL CAMERA

BACKGROUND OF THE INVENTION

1. Field of the Invention

The present invention relates to an intra-oral camera for use in dentistry according to the preamble of claim 1.

2. Related Technology

In dentistry, optical photographs of the teeth to be examined are often produced for diagnostic reasons, since any required therapeutic measures can be conveyed to the patient more effectively on the basis of an optical image. The so-called intra-oral cameras used for this purpose are in this case used both for macro photographs, i.e. for example for photographing cavities of an individual tooth, and for a range of photographs from photographs of individual teeth to a full-face photograph. In the past, the use of a constant focal length was provided both for intra-oral and for extra-oral applications, wherein preferably a very short focal length was used, as this was the best solution for intra-oral applications on account of the naturally limited space conditions. Nevertheless, in cheaper optical systems, such a short focal length causes marked distortion; this led to very limited usability of the system for full-face photographs. Ultimately, a camera of this type allows only a very limited observation range to be sharply imaged.

In order to improve the quality, of the optical representations both in the close and in the remote range, it was also known to carry out an adjustment of the image plane of the photographing unit or the image sensor in accordance with the selected photographing situation. This adjustment could be carried out for example manually via the focusing of the imaging system, for example by displacing a group of lenses along the optical axis. Alternatively thereto, it is also possible to carry out the focusing, i.e. the adjustment of the position of the image onto the sensor plane, in an automated manner, wherein the contrast determination of the image signal can be used as an evaluation variable.

The region to be observed by the camera is lit up conventionally with the aid of an illumination unit which is integrated into the camera or attached to the input of the camera in a suitable manner. In close-up photographs of this type, much more reflected light strikes the image sensor on account of the marked reflections of the teeth in conjunction with the short distance of the object in cameras used intra-orally. For this reason, it is beneficial to vary the diaphragm or aperture of the optical system as a function of the available light in order to increase what is known as the depth of sharpness. In this connection, EP 1 058 860 describes a dental camera in which there is a fixedly predefined coupling between the diaphragm and focus via a functional element. Nevertheless, the drawback of this known fixed coupling of the diaphragm opening to the position of the focus lens is the inability of the system to carry out an optimum adaptation to the prevailing conditions. Thus, a fixedly predefined diaphragm in the macro range often does not lead, on account of the different absorption of light of the objects to be photographed, to optimum exposure of the sensor. The absorption of amalgam is for example several times higher than the absorption of dentine. For sharp representation of depth cavities in dentine, a small diaphragm diameter, for example, is therefore advantageous for a high depth of sharpness. Nevertheless, if this macro setting is used to examine a highly absorbing amalgam filling, the signal detected by the sensor has to be strongly boosted on account of the high absorption of the amalgam, as a result of which the signal-to-noise ratio is impaired. If a larger diaphragm diameter is used, on the other hand, local "overexposure" of the image can occur, so that individual pixels of the image recorder become saturated; ultimately, this prevents the object from being sufficiently recognizable.

SUMMARY OF THE INVENTION

The present invention accordingly improves over the solutions known in the art for implementing intra-oral cameras in order to allow optimum photographing conditions for all situations in which photographs are taken.

Accordingly, the invention provides an intra-oral camera with an imaging system for imaging the object located before a viewing window of the camera onto a photographing unit, the imaging system having at least one focusing unit for setting a suitable focus and also a diaphragm unit for forming a variable diaphragm, wherein the diaphragm is set independently of the focus set by the focusing unit.

The solution according to the invention proposes, in contrast to the prior art of EP 1 058 860, that the setting of the diaphragm is not rigidly coupled to the focus of the imaging system of the camera, but that instead the variable diameter of the diaphragm can be set independently. This allows greater flexibility with regard to the photographing conditions, thus ensuring that the sensor or the photographing unit in general can be optimally exposed at all times.

The present invention accordingly proposes an intra-oral camera with an imaging system for imaging the object located before a viewing window of the camera onto a photographing unit, the imaging system having at least one focusing unit for setting a suitable focus and also a diaphragm unit for forming a variable diaphragm, and the diaphragm being set according to the invention independently of the focus set by the focusing unit.

The diaphragm is set preferably automatically. The intra-oral camera according to the invention can have for this purpose a control unit for automatically activating the diaphragm unit. The activation can in this case be carried out on the basis of an output signal provided by the photographing unit. Nevertheless, alternatively or additionally thereto, provision may also be made for the camera to have input elements for manually selecting a diaphragm.

The diaphragm unit itself can for example have a motor-driven iris or cat's-eye diaphragm allowing almost stepless setting of the diaphragm opening. Nevertheless, it is also alternatively possible to provide a first diaphragm having a first diaphragm diameter and also a second diaphragm which can be selectively introduced into the beam path of the imaging system and has a second diaphragm diameter which is smaller than the first diaphragm diameter. A large or a small diaphragm can then be selectively set with the aid of the second diaphragm which can be mounted movably, in particular displaceably, rotatably, tiltably or pivotably. Furthermore, the diaphragm unit can also have an optical element which can be selectively introduced into the beam path of the imaging system and with the aid of which the diaphragm is set. The end position of the diaphragm can be fixed in this case with the aid of permanent magnets.

According to a preferred embodiment of the camera according to the invention, the focusing unit is also activated automatically. Again, the activation can be carried out by an appropriate control unit on the basis of an output signal provided by the photographing unit. Furthermore, the use of a sensor for determining the position of an object or the manual selection of the focus setting with the aid of appropriate input elements would also be conceivable.

The focusing unit can then for example have a lens or group of lenses, which can be adjusted in the direction of the optical axis, or be configured in such a way that the photographing unit is varied with regard to its position.

Another development of the camera in accordance with the invention consists in the fact that the focal length can additionally also be provided with the aid of a group of adjustable lenses. This makes it possible to switch between macro photographs and full-face photographs.

Finally, the present invention also provides a camera which provides optimum results with regard to its imaging properties for a broad range of photographing situations in the dental sector.

BRIEF DESCRIPTION OF THE DRAWINGS

The invention will be described hereinafter in greater detail with reference to the appended drawings, in which.

DETAILED DESCRIPTION

Figure 1:
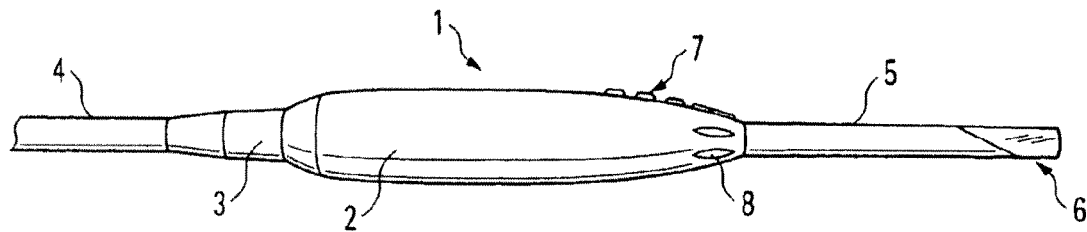
FIG. 1 is a view of an intra-oral camera in accordance with the invention.

The intra-oral camera in accordance with the invention, which is provided generally with reference numeral 1 in FIG. 1, has an elongate hand piece or gripping piece 2 in which the basic electronics of the camera are arranged. At the back, the gripping piece 2 is connected via a connector 3 to a supply/data transmission pipe 4 leading to a central unit (not shown). Via this pipe 4, which can contain a USB cable for example, on the one hand the supply of power to the camera 1 is ensured; furthermore, image information can also be transmitted from the camera 1 to a screen and presented. Wireless transmission of the image data to a monitor or to the central unit in general would also be conceivable.

A probe-shaped camera head 5, which contains the light entrance or viewing window 6 for the camera optics, is located at the leading end of the gripping body 2. For ergonomic reasons, the viewing window 6 is arranged in this case not at the end side of the head 5, but on the lateral surface thereof. The image is then deflected accordingly by means of optical elements which will be described in greater detail hereinafter. Furthermore, an illumination unit (not shown in greater detail) is arranged in the head region to light up the region to be observed. Possibilities for implementing this illumination unit will be described hereinafter.

Various manual input elements 7 and 8, with the aid of which the camera 1 can be operated, are located on the gripping body 2 itself. Some of the elements 7 and 8 respectively can in this case be provided for controlling the diaphragm and also the focus. Still other elements can serve to initiate the storage of a current camera image or to switch between a live image mode and a still image mode. Appropriate LEDs, which indicate the current camera setting, can be associated with the input elements 7, 8. The handle or gripping body 2 has preferably a somewhat larger diameter and thus offers sufficient space for the various electronic units.

The various optical and electronic components of the camera in accordance with the invention are illustrated schematically in FIG. 2 and will be described hereinafter. The photographing unit 10 used in this case is a digital image-recording element, for example in the form of a CCD or CMOS chip. The object located before the viewing window 6 of the camera 1 is then imaged onto this chip 10 with the aid of optical means, use being made for this purpose on the one hand of a wedge-shaped prism 11 for image deflection, which defines the viewing direction, and also on the other hand of an imaging system 12. The imaging system 12 has to begin with a plurality of lenses 13 arranged stationarily in the attachment 5 and also a zoom lens 14 which is adjustable with regard to its position in the longitudinal axis. The focal length of the imaging system can be set in accordance with the position of the lens 14, the setting being carried out—as will be described hereinafter in greater detail—preferably with the aid of an appropriate motor controller.

Arranged downstream of the zoom lens 14 is a diaphragm unit 15, the axial position of which is fixed and with the aid of which a size- or diameter-variable diaphragm is formed. Finally, a focusing unit 16 is also arranged between the diaphragm unit 15, which is preferably arranged at a point of intersection of the beam path with the optical axis, and the chip 10 in order to sharply image the image of the object located before the viewing window 6 of the camera 1 onto the chip 10.

Figure 2:
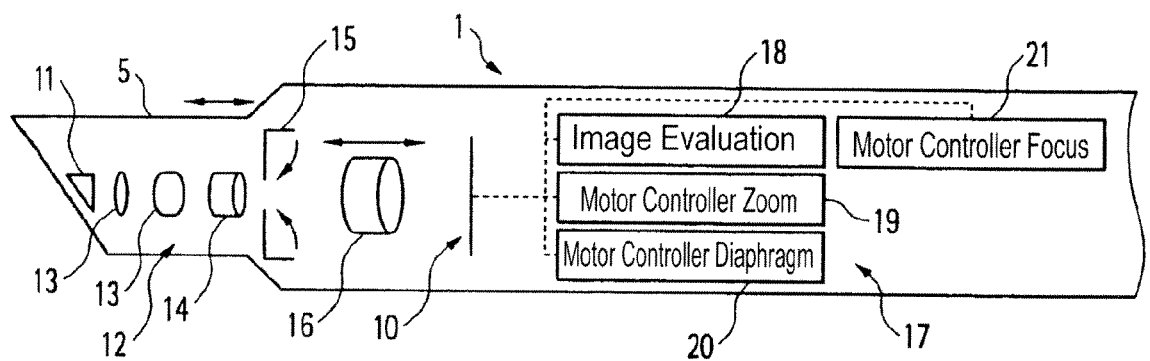
FIG. 2 is a schematic illustration of the various components of the camera in accordance with the invention in accordance with a first exemplary embodiment.
Figure 3:
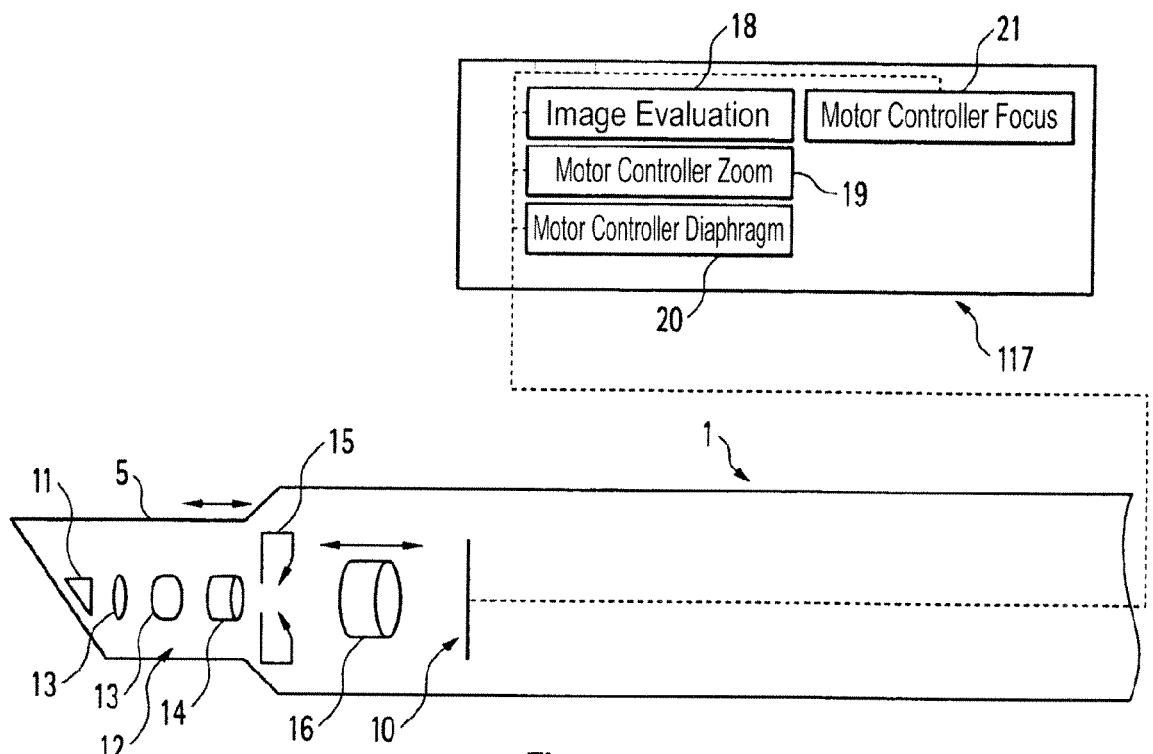
FIG. 3 is a variant of the illustration from FIG. 2.

The various components of the imaging system are activated preferably with the aid of appropriate control units which are arranged, in the variant according to FIG. 2, likewise in the gripping sleeve of the camera 1. The electronics 17 of the camera 1 comprise in this case in the first place an image evaluation unit 18, the information of which is used by the further control units. These further control units are on the one hand the motor controller zoom 19 for activating the zoom lens 14, the motor controller diaphragm 20 for activating the diaphragm unit 15 and also the motor controller focus 21 for activating the focusing unit 16. In this case, in accordance with the alternative illustration in FIG. 3, it is also possible to transfer the electronics 117 out of the camera 1, for example to arrange them in the aforementioned central means.

Preferably, provision is made for the camera 1 to be focused automatically. For this purpose, provision may for example be made for the contrast range of the image recorded by the chip 10 to be determined and evaluated. The focusing unit 16 is then adjusted with continuous contrast calculation until a maximum contrast range is achieved. As experience teaches that maximum contrast is achieved in focused setting, a good sharpening of the image can be achieved in this way.

In this connection, it should be borne in mind that if the change in the distance of the object from the camera should produce an unsharp image on the image recorder, it is uncertain in which direction it is necessary to move in order to obtain a sharp image again. The focusing means 16 therefore preferably moves in accordance with a fixed program. On the one hand, all possible positions can be assumed, the image sharpness value (for example contrast function) resulting from the data of the image recorder being computed in each position by means of a microcontroller, FPGA or DSP. On account of the functional dependency of the setting of the focusing means 16 and the image sharpness value determined in each case, the optimum of the image sharpness can then be determined and the focusing means 16 can be moved into the associated desired position.

Another possibility for finding the best possible value for the sharp setting of the image consists in adjusting the focusing means 16, starting from the respective position, and in searching for the direction which causes an improvement in the image sharpness. This may be continued until the optimum is achieved (steepest descent or hill-climbing algorithm).

As an alternative to these variants, it would also be conceivable to detect the distance from the object to be observed in the image centre with the aid of a sensor. Depending on what object distance was determined, an appropriate setting of the focusing means 16 can then be carried out. Furthermore, a discrete focus setting could also be selected with the aid of the operating elements 7 and 8 respectively, which are located on the camera 1, and then be approached with the aid of the motor controller 21. Finally, in addition, the intensity of the brightness signal can also be taken into account in the automatic focusing.

Figure 4:
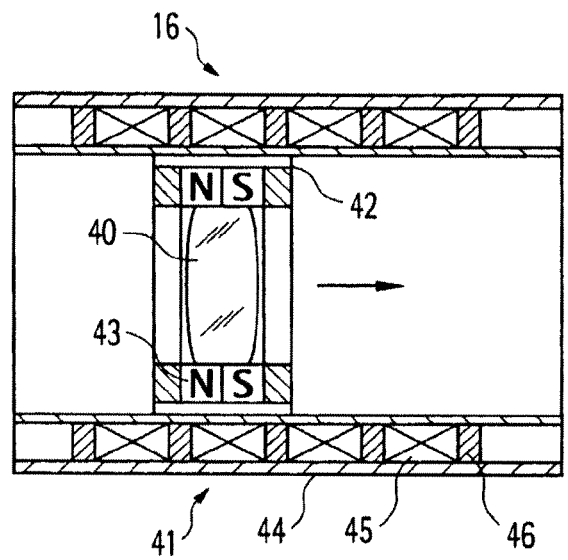
FIG. 4 shows an exemplary embodiment of a motor for varying the focus setting.

A preferred embodiment of a focusing means 16 is illustrated in FIG. 4. In this case, a lens 40 or a group of lenses is displaced along the optical axis with the aid of a special drive. The lens 40 or group of lenses is in this case moved via a linear stepping drive 41 and is arranged for this purpose on a guide element 42 having magnetic rings 43. Furthermore, a stator, which has a yoke 44, magnetic coils 45 and also ferromagnetic rings 46, is embodied in the longitudinal direction of the drive 41. The appropriate application of voltage to the coils 45 generates a force which acts in the longitudinal direction and via which the guide element 42 can be displaced with the lens 40 in a simple manner. The coils 45 are activated in this case, as already mentioned, by the appropriate activation unit 21 of the camera electronics 17.

The linear drive illustrated in FIG. 4 for focus setting is a particularly preferred embodiment of the present invention, as it is an extremely compact mechanism for varying the focus position. The design of this micro stepping drive allows it to be readily integrated into the camera head 5. The micro stepping drive saves the user of the camera from having to sharpen the image by hand in a manner which is awkward as a result of friction. Furthermore, on account of the low mass of the rotor and the short distance of travel, the above-described process for automatic focusing may be carried out in less than one second, so that the user obtains a sharp image without significant delay. The fact that only a small number of lens positions have to be approached, on account of the operation as a stepping motor, is helpful in this connection.

Nevertheless, it would also alternatively be conceivable to insert or to fold optical plates into the beam path of the camera in order to vary the focus position. Furthermore, the chip 10 itself could also be displaced along the optical axis of the camera 1. The focusing can in this case be carried out in discrete steps or continuously, wherein provision may also be made, in addition to the automatic focusing, to manually deactivate the focusing temporarily if a specific setting is explicitly preferred.

The variable diaphragm unit 15 serves to increase the depth of sharpness of the camera 1 in intra-oral use. For optimum handling of the camera 1 by a user, provision is in this case preferably made for the diameter of the diaphragm to be set automatically and in a situation-related manner, in particular independently of the setting of the focusing means 16. In this case, the diaphragm unit 15 is arranged in the optical beam path of the camera 1 in such a way that, depending on the size of the diaphragm opening, it limits the brightness of the image, but does not restrict the field angle, i.e. the size of the object field that can be imaged by the optical system.

The automatic setting is achieved, again, via the evaluation of the input signal by the CCD or CMOS chip 10. If there is sufficient light, a diaphragm having a small diaphragm diameter is in this case set in order to increase the sharpness of depth. Experience teaches that this is the case in the macro range on account of the short distance from the light outlet and object field plus the strong reflection of the teeth. If, nevertheless, highly absorbing objects, such as for example amalgam or the like, are photographed, a diaphragm having a larger diaphragm diameter is automatically selected on account of the weaker input signal of the image sensor 10. This ensures that the brightness value which is ultimately achieved is adapted in an optimal manner to the regulating range of the image recorder. In this case, provision may again be made for it to be possible also deliberately to select by hand a specific diaphragm setting with the aid of the input elements 7.

The macroscopically conventional method for steplessly altering the diameter of the diaphragm is embodied by the known "iris diaphragm". The opening is, depending on the quality of the iris, almost circular in all sizes. Iris diaphragms usually consist of a plurality of blades which are at the same time turned outwards or inwards. All the blades are in this case mounted on their own shaft and joined together by a ring via a respective further shaft. The common movement is generated in this way.

A simplified variant of the iris diaphragm is what is known as the cat's-eye diaphragm in which two blades with triangular incisions are moved relative to each other in order to vary the size of the opening. The drive has to provide in this case a movement perpendicular to the direction of light. A cat's-eye diaphragm of this type is much easier to produce, although the shape of the diaphragm often restricts the image in an undesirable shape. Furthermore, the overall space for the diaphragm unit 15 in the camera 1 is very limited; this is why the solutions described hereinafter for configuring the guides and drive for adjusting the diaphragm opening differ from macroscopic solutions.

In contrast to the stepless diaphragm systems described hereinbefore, diaphragms with stepwise alteration of the diaphragm diameter are provided only with the required diaphragm diameters. In operation, these diaphragms then switch the opening as required. However, intermediate steps are not possible in this case. In the simplest case, a large fixed diaphragm is covered by a smaller diaphragm. For movement, simple linear, rotatory or tilting movements may be used. Little friction occurs in the case of suitable bearing arrangements. The required drive power is correspondingly low.

Figure 5:
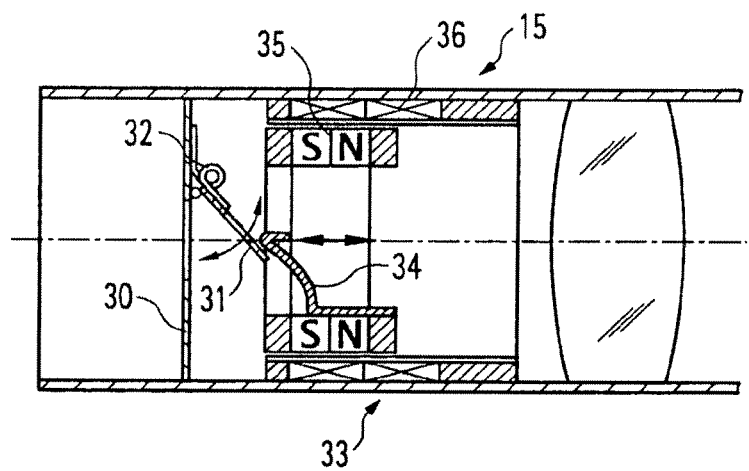
FIG. 5 shows an exemplary embodiment of a variable diaphragm unit configured in accordance with the invention.

A first preferred embodiment of a diaphragm unit 15 is accordingly illustrated in FIG. 5. The illustrated embodiment allows in this case the selection between two different diaphragm settings, a first diaphragm 30 having a large diaphragm opening being fixedly arranged on the one hand in the beam path of the imaging system. Furthermore, a second diaphragm 31 having a smaller diaphragm diameter can be introduced into the beam path if required. The second diaphragm 31 is in this case mounted so as to be able to pivot via a hinge 32, which is formed by a spring, and can be folded in with the aid of a further linear drive 33. For this purpose, an actuating element 34 is arranged on a guide part 35 with permanent magnetic rings. The permanent magnetic rings are in turn surrounded by a stator with a plurality of stator windings 36. The guide element 35 can then be displaced in the longitudinal direction by appropriate activation of the stator windings 36 and the second diaphragm 31 can be selectively folded in or out as a result. Again, this electromagnetic mechanism is distinguished by its compact configuration allowing an arrangement or integration into the camera 1.

Further possibilities for forming a two-stage diaphragm of this type are illustrated schematically in FIGS. 6a to 6e. In this case, the movements are in the variants of FIGS. 6a and 6b linear movements, in FIGS. 6c, 6d and 6e tilting or rotational movements, diaphragm elements 37 being introduced in all of the variants into the beam path of the camera in order to selectively form a large or a small diaphragm opening. In principle, various energy conversion methods may be used for carrying out the movement, wherein piezo actuators, shape memory or bimetallic drives and also magnetostrictive or electromagnetic drives are possible on account of the low overall space. What matters is that the diaphragms are exchanged for the underlying application sufficiently rapidly that the observer does not notice this or perceives only a change in brightness. The high voltages required for piezo drives largely rule these out. Magnetostrictive drives require a comparatively large overall space; drives comprising bimetals or shape memory alloys have a long dead time on account of the necessary change in temperature, so that the drives are primarily electromagnetic drives—for example corresponding to the type according to FIG. 5.

Permanent magnets may expediently be used for fixing the end positions of the diaphragm elements 37. It is possible to optimize the drive in this case as a result of the broad avoidance of friction and the restriction to short distances and low moved masses. FIGS. 7a to 7d show in this case possible embodiments for a tilting drive in which the end stop of the diaphragm element 37 is fixed as a result of the use of permanent magnets. Small air gaps are recommended in this case in order both to keep down the magnetomotive force for the switching pulse and to generate sufficient forces for the movement.

Figure 6:
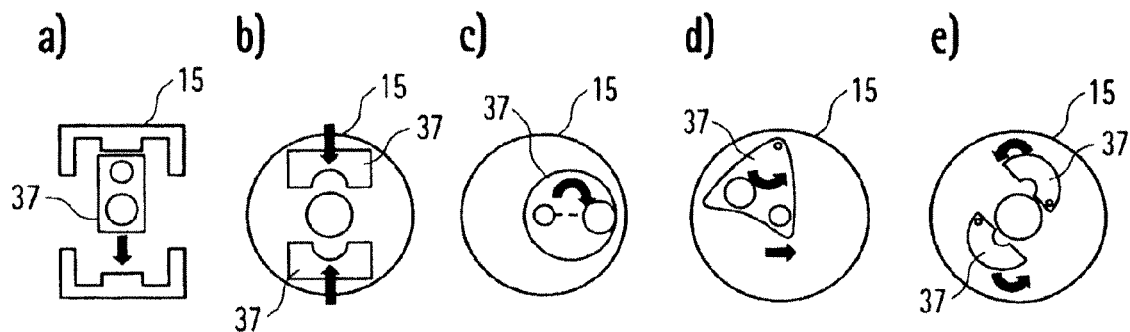
FIGS. 6a to 6e show variants for forming a two-stage diaphragm unit.
Figure 7:
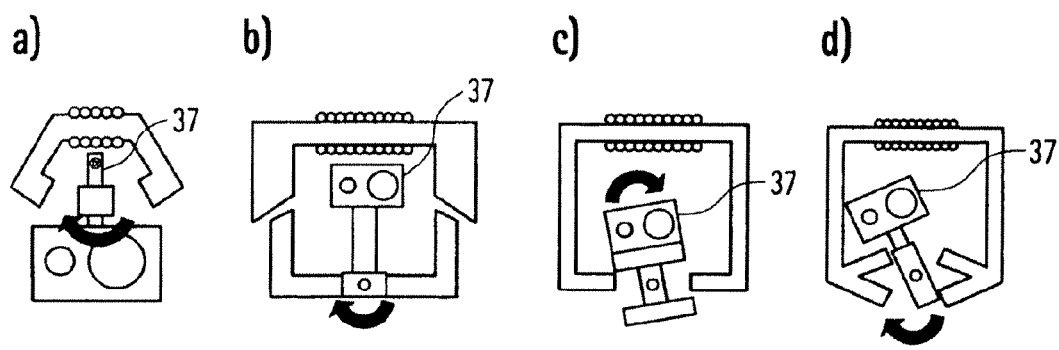
FIGS. 7a to 7d show further possibilities for implementing a tilting drive for forming a two-stage diaphragm unit.

Alternatively to the embodiments illustrated in FIGS. 5 to 7, use could also be made of a motor-driven iris diaphragm allowing stepless setting of the diameter of the diaphragm. Although this further improves the optical properties of the camera 1, this mechanism is more complex to implement. Furthermore, the insertion of optical plates, through which the focus position or the aperture of the optical system is varied, into the beam path would be conceivable.

Figure 8:
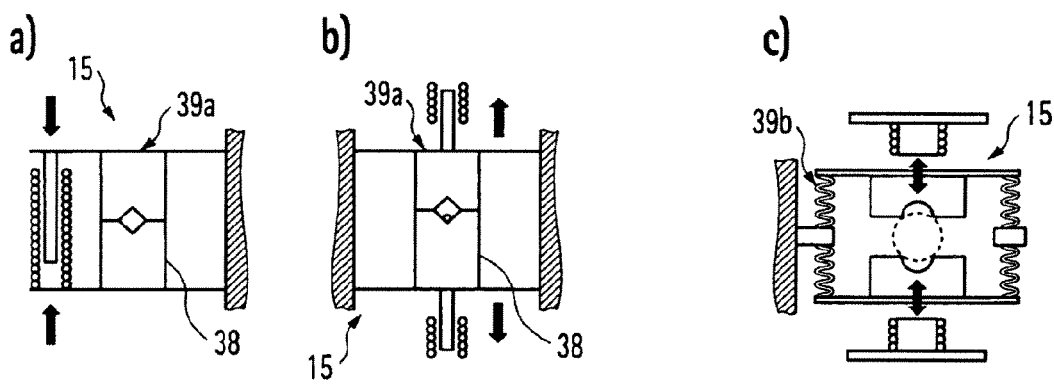
FIGS. 8a to 8c show possibilities for forming a steplessly adjustable diaphragm unit.

Further possibilities for implementing a steplessly adjustable diaphragm are further illustrated in FIGS. 8a to 8c, the combination of a movement of a cat's-eye diaphragm 38 via bending beams 39a (FIGS. 8a and 8b) or with the aid of a tension spring mechanism 39b (FIG. 8c) being provided in each case with an electromagnetic drive.

The zoom lens 14 can be adjusted by a linear drive in the same manner as the adjustment of the focusing unit 16. A variable focal length may in this way be achieved for the optical system of the camera 1. Nevertheless, this additional setting possibility could also be dispensed with. If, however, it is possible to change the focal length, this is carried out preferably as a function of the focus position. A short focal length in conjunction with a small diaphragm diameter for the intra-oral region at a short object distance allows in this case a good overview of the object field at a maximum depth of sharpness. A long focal length, on the other hand, in conjunction with a larger diaphragm diameter in extra-oral use allows a distortion-free, natural representation of the object if total photographs of the patient's set of teeth or full-face photographs are desired.

Ultimately, the above-described optical elements of the camera in accordance with the invention create optimum imaging conditions for any photographing situation. Compared to previously known systems, the intra-oral camera in accordance with the invention can thus be used much more flexibly and can be utilized in a broad range of situations in order to produce high-quality images.

Figure 9:
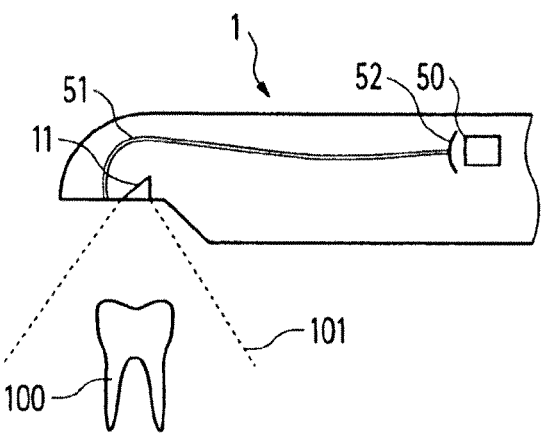
FIGS. 9 to 11 show various variants for configuring the illumination of the intra-oral camera in accordance with the invention.
Figure 10:
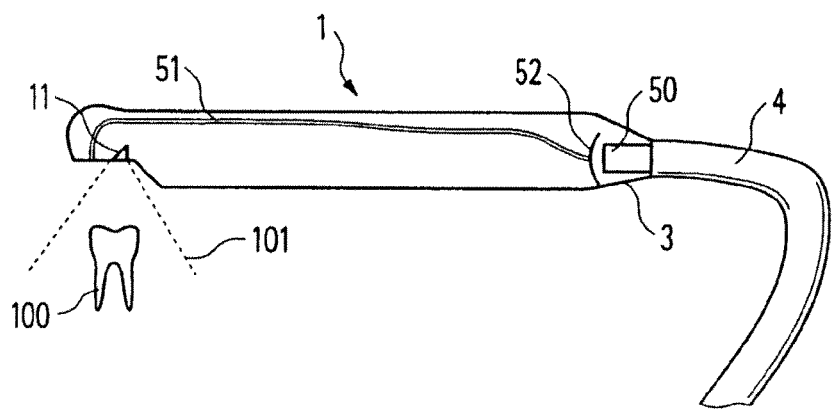
Figure 11:
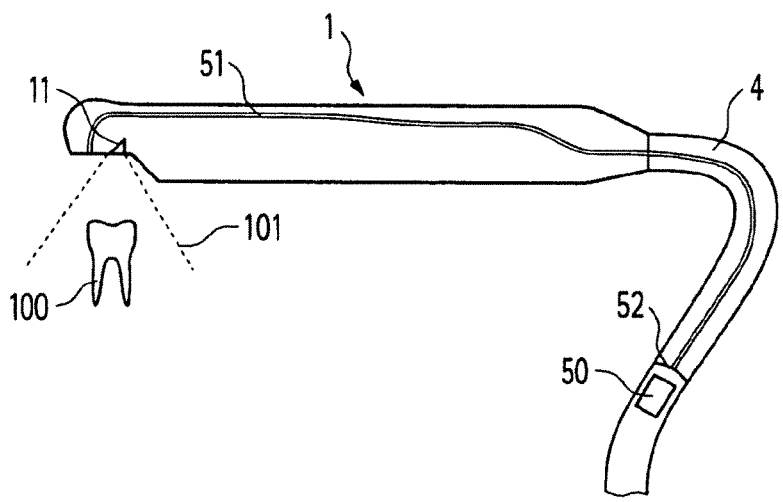

FIGS. 9 to 11 show variants of the camera 1 in accordance with the invention, different possibilities being presented for lighting up the viewing region 101 of the prism 11. It is essential that the viewing region 101 be lit up in as nearly optimal a manner as possible in order to be able to detect in a suitable manner objects arranged within the region, for example the illustrated tooth 100, by the CCD or CMOS chip 10. For the sake of clarity, the above-described optical elements of the imaging system have not been shown. Only the components of the camera 1 that are responsible for illumination are shown.

In all three variants, the light source used is preferably an LED, wherein the LED may be either a white light LED or an LED arrangement consisting of different-colored LEDs which jointly emit a white mixed light. The light from this light source 50 is then guided, preferably via a light guide 51, to the camera head and directed from there onto the viewing region 101 of the prism 11. In accordance with the three illustrated variants, the light source 50 can in this case be arranged within the gripping sleeve 2, in the connection region 3 or in the supply pipe 4. The light from the light source 50 is coupled into the light guide 51 in this case preferably with the aid of a schematically indicated reflector 51 or other optical elements. Direct coupling of light into the light guide 51, which is formed preferably by a flexible fibre bundle, would also be conceivable. For better coupling-in of light, the flexible fibre bundle is in this case fused at the ends. The transportation of light towards the camera head with the aid of the light guide 51 or via a light guide rod has in this case the advantage of allowing the size of the camera head to be minimized, as a result of which the intra-oral freedom of movement of the camera 1 is additionally increased.

Figure 12:
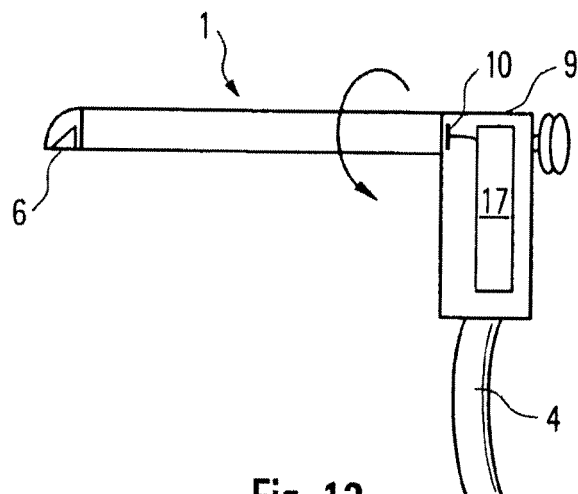
FIG. 12 shows a further variant of the intra-oral camera in accordance with the invention.

Another development of the camera 1 in accordance with the invention is illustrated in FIG. 12. In this case, the front end region with the viewing window 6 and the optics located therein is rotatable, thus allowing physiologically comfortable handling of the camera 1 both for lower and for upper jaw photographs. A handle 9 with the integrated camera electronics 17 and also the image recording sensor 10 is in this case fixed and intended for perpendicular holding. The optics themselves engage preferably in 90° or alternatively in 180° increments. The position of the optics is limited by a mechanical stop to at most 270°. The position of the optics is furthermore detected preferably automatically, so that in upper jaw photographs the video image is represented automatically reflected via the camera electronics. Alternatively, the position of the optics is detected with the aid of a special sensor and embedded into the video signal as information. The live video is in this case shot via an appropriate software package.

Figure 13:
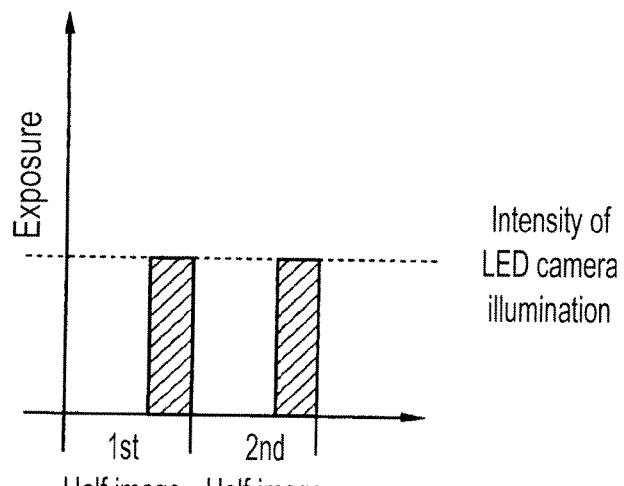
FIGS. 13 and 14 show the procedure for exposure in two different photographing modes of the camera.
Figure 14:
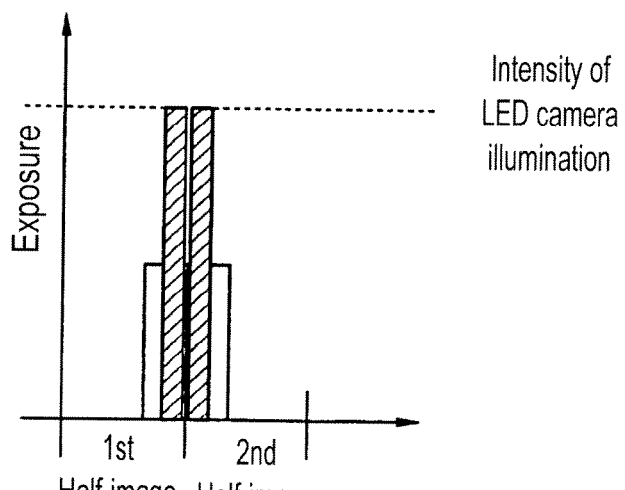

Finally, FIGS. 13 and 14 show two different variants for activating the illumination of the camera, on the one hand for a live image mode (FIG. 13) and on the other hand for a still image mode (FIG. 14). The illumination is operated preferably in a pulsed manner and is in this case synchronized to the shutter of the camera. When switching over to still image mode, the length of the shutter time is in this case retained; nevertheless, the exposure time is postponed to the end of the first half-image and to the start of the second half-image, as FIG. 11 shows. The amount of light for exposure of a half-image, to be precise the integral of the illumination intensity over the pulse duration, is in this case to remain the same when switching over from the live to the still image. A color shift of the recorded image as a consequence of the higher LED powering in pulsed mode is in this case compensated for; this can be carried out by appropriate manipulation of the recorded image data.

Viewed globally, the invention thus proposes a strategy for a novel intra-oral camera which has clear advantages over previously known solutions with regard to its imaging properties. As a result of the developments with regard to illumination and also the activation of illumination, an optimum photographing quality can in this case be achieved both in live image mode and in still image mode.

The invention claimed is:

1. Intra-oral camera comprising an imaging system for imaging an object located before a viewing window of the intra-oral camera onto a photographing unit, the imaging system comprising:
   at least one focusing unit for setting a suitable focus;
   a diaphragm unit for forming a variable diaphragm, wherein the diaphragm is set independently of the focus set by the focusing unit; and
   a control unit for automatically varying a diameter of the diaphragm unit, wherein the control unit is configured to automatically increase the diameter of the diaphragm unit on occurrence of one of first and second conditions, the first condition being that at least one output signal is greater than a signal level, the second condition being that the at least one output signal is less than the signal level, the control unit is further configured to decrease the diameter of the diaphragm unit on occurrence of another one of the first and second conditions, and the photographing unit provides the at least one output signal to the control unit.

2. Intra-oral camera according to claim 1, wherein the intra-oral camera comprises input elements for manually selecting a diaphragm.

3. Intra-oral camera according to claim 1, wherein the diaphragm unit comprises a motor-driven iris or cat's-eye diaphragm for stepless diaphragm setting.

4. Intra-oral camera according to claim 3, wherein the diaphragm is set with an aid of using bending beams or tension springs.

5. Intra-oral camera according to claim 1, wherein the diaphragm unit comprises a first diaphragm having a first diaphragm diameter and a second diaphragm that can be selectively introduced into a beam path of the imaging system and that has a second diaphragm diameter that is smaller than the first diaphragm diameter.

6. Intra-oral camera according to claim 5, wherein at least the second diaphragm is movably mounted.

7. Intra-oral camera according to claim 6, wherein an end position of the second diaphragm is fixed with the aid of permanent magnets arranged at holding points.

8. Intra-oral camera according to claim 6, wherein at least the second diaphragm is displaceably, rotatably, tiltably, or pivotably mounted.

9. Intra-oral camera according to claim 5, wherein the diaphragm unit comprises an optical element that can be selectively introduced into the beam path of the imaging system for varying the diaphragm.

10. Intra-oral camera according to claim 9, wherein the focusing unit comprises an optical element that can be selectively introduced into the beam path of the imaging system for varying the focus setting.

11. Intra-oral camera according to claim 1, comprising a control unit for automatically activating the focusing unit.

12. Intra-oral camera according to claim 11, wherein the focusing unit is activated on the basis of an output signal provided by the photographing unit.

13. Intra-oral camera according to claim 11, comprising a sensor for determining the distance of the object.

14. Intra-oral camera according to claim 1, comprising input elements for manually selecting a focus setting.

15. Intra-oral camera according to claim 1, wherein the focusing unit comprises a lens or group of lenses that can be adjusted in the a direction of an optical axis.

16. Intra-oral camera according to claim 1, wherein the focusing unit comprises means for adjusting the photographing unit.

17. Intra-oral camera according to claim 1, comprising a group of lenses that can be adjusted in the direction of the longitudinal axis of the imaging system for varying the focal length.

18. Intra-oral camera according to claim 1, comprising an elongate gripping piece.

19. Intra-oral camera according to claim 18, wherein the gripping piece is divided into a first region forming a handle and a second region containing at least the viewing window, the second region being rotatable in relation to the first region.

20. Intra-oral camera according to claim 1, wherein the intra-oral camera is operable in a live image mode and in a still image mode.

21. Intra-oral camera according to claim 1, comprising an illumination unit for illuminating the object to be observed.

\* \* \* \* \*